(12) United States Patent
Wagner et al.

(10) Patent No.: US 9,212,747 B2
(45) Date of Patent: Dec. 15, 2015

(54) SEALING CONFIGURATION WITH METAL-COATED STRUCTURE

(75) Inventors: Joachim Wagner, Waldbronn (DE); Hans-Georg Haertl, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 460 days.

(21) Appl. No.: 13/020,561

(22) Filed: Feb. 3, 2011

(65) Prior Publication Data

US 2011/0186497 A1    Aug. 4, 2011

(30) Foreign Application Priority Data

Feb. 4, 2010 (GB) .................................. 1001782.0
Jun. 28, 2010 (GB) .................................. 1010816.5

(51) Int. Cl.
*F16J 15/12* (2006.01)
*G01N 30/60* (2006.01)
*B01D 15/22* (2006.01)

(52) U.S. Cl.
CPC ........... *F16J 15/128* (2013.01); *G01N 30/6026* (2013.01); *B01D 15/22* (2013.01)

(58) Field of Classification Search
CPC ..... G01N 30/6026; F16J 15/128; B01D 15/22
USPC ........ 210/635, 656, 198.2; 277/602; 285/335, 285/374
See application file for complete search history.

(56) References Cited

U.S. PATENT DOCUMENTS

| | | | |
|---|---|---|---|
| 1,731,404 A | 10/1929 | Wetherill | |
| 2,127,372 A * | 8/1938 | Victor et al. | 277/592 |
| 2,211,247 A | 8/1940 | Victor et al. | |
| 3,093,581 A * | 6/1963 | Cordes et al. | 210/444 |
| 3,690,685 A * | 9/1972 | Porner et al. | 277/653 |
| 4,293,116 A * | 10/1981 | Hinrichs | 251/173 |
| 4,982,597 A | 1/1991 | Berger | |
| 5,421,594 A | 6/1995 | Becerra | |
| 5,785,322 A | 7/1998 | Suggs et al. | |
| 6,250,644 B1 * | 6/2001 | Diez et al. | 277/595 |
| 6,994,356 B2 | 2/2006 | Veiga | |
| 2002/0017763 A1 * | 2/2002 | Udagawa et al. | 277/592 |
| 2004/0004327 A1 | 1/2004 | Veiga | |
| 2005/0269789 A1 * | 12/2005 | Kameyama | 277/592 |
| 2007/0013145 A1 * | 1/2007 | Detmann et al. | 277/593 |
| 2007/0035939 A1 * | 2/2007 | Wallace et al. | 361/816 |
| 2007/0228668 A1 * | 10/2007 | Dempsey et al. | 277/627 |
| 2008/0099070 A1 * | 5/2008 | Luongo et al. | 137/15.18 |
| 2008/0280040 A1 * | 11/2008 | Barrall et al. | 427/256 |
| 2011/0031706 A1 * | 2/2011 | Komukai et al. | 277/653 |
| 2011/0186497 A1 * | 8/2011 | Wagner et al. | 210/198.2 |

FOREIGN PATENT DOCUMENTS

| | | |
|---|---|---|
| EP | 1577012 | 9/2005 |
| EP | 1995461 | 11/2008 |
| GB | 1535441 | 12/1978 |
| GB | 2433577 | 6/2007 |

OTHER PUBLICATIONS

Wikipedia definition of Hastelloy undated.*
First Office Action for Chinese Patent Application No. 201110035183.7 mailed Aug. 18, 2014.

* cited by examiner

*Primary Examiner* — Ernest G Therkorn

(57) ABSTRACT

A sealing configuration is configured for sealingly coupling a first fluid flow path of a first device to a second fluid flow path of a second device. The sealing configuration comprises a contact surface comprising a structure configured for increasing a surface pressure when coupling the first device to the second device. The contact surface comprises a metal coating configured for increasing sealing.

16 Claims, 3 Drawing Sheets

SEALING CONFIGURATION WITH METAL-COATED STRUCTURE

This application claims priority from UK Patent Application, No. GB 1001782.0 filed 4 Feb. 2010 and from GB 1018016.6 filed 28 Jun. 2010, which are incorporated by reference in their entirety.

BACKGROUND

The present invention relates to sealingly coupling of components or devices, in particular in a high performance liquid chromatography application.

U.S. Pat. No. 1,731,404 A discloses a flat orifice plate which has a central orifice and which is circular in form and made of Monel metal. Entirely surrounding the outer portion of the plate is a gasket member consisting of a cylindrical shell of yielding metal, such as copper, and a yielding material such as asbestos interposed between the side portions of said shell and thus between the adjacent faces of the orifice plate.

U.S. Pat. No. 2,211,247 A discloses a metal gasket with sealing coating, which may be of digested elaterite or some other resilient organic material and works its way into depressions between ridges of the gasket. Upon application of the gasket between cylinder head and block, the resilient coating is squeezed down into the depressions, allowing the high or sharp points of the protuberances to contact the metal of the adjacent elements. These points are then either pressed down or distorted slightly.

U.S. Pat. No. 5,421,594 A discloses a corrugated gasket encapsulated with a graphite material, such as an expanded graphite with adhesive backing.

U.S. Pat. No. 5,785,322 A shows a gasket for flange connections and having concentric deformable ridges.

EP 1995461 A1 discloses leakage prevention in a compressor utilized in a refrigeration cycle. A gasket is formed by covering the two surfaces of a metal plate respectively with rubber layers, and has bead portions formed as projections cresting toward a cylinder block.

U.S. Pat. No. 6,994,356 B2 discloses a gasket seal for flanges of piping and equipment. A sealing ring comprises an outer contour surface, an inner contour surface, a lower surface, and an upper surface. The lower surface and the upper surface, respectively, consist of respective lower and upper prolongations of the outer contour surface and the inner contour surface, and have a serrated profile (concentric grooves) and a sealant coating of a graphite or polymeric material.

In high performance liquid chromatography (HPLC), a liquid has to be provided usually at a very controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid.

In modern HPLC with pressures rising up to 100 MPa and beyond, life time of components such as seals becomes critical.

GB 2433577 B discloses a gasket for an HPLC instrument having a fluid containing conveying device for receiving and discharging fluids. The device comprises a housing having a chamber for containing a fluid. The housing has a first gasket receiving surface for receiving a gasket. A gasket is formed of a deformable material and has first and second abutment surfaces. The first abutment surface is received on a first gasket receiving surface, and the second abutment surface is received by a chamber closing piece for closing the chamber and having a second gasket receiving surface. At least one of the first and the second gasket receiving surfaces of the chamber closing piece have a retaining groove with at least one edge. Compression means for compressing the gasket are deforming the material such that the gasket is pressed into the retaining groove and gripped by the edge of the cavity to prevent gasket movement.

For sealing valves, filters or the like when being fixed to an HPLC pump head, the applicant Agilent Technologies has introduced a solid gold seal (part number 5001-3707) as disclosed e.g. in GB 1535441 A or under http://www.chem.agilent.com/Library/Support/Documents/A03665.pdf, which has been reliably used over many years.

With increasing pressure of 500-2000 bar as applied in modern HPLC, sealing properties of abutting components in the fluid flow path and in particular seals used between such abutting components become more and more critical.

SUMMARY

It is an object of the invention to provide an improved sealing, in particular suitable for high pressure HPLC applications.

According to an embodiment of the present invention, a sealing configuration is provided configured for sealingly coupling a first fluid flow path of a first device to a second fluid flow path of a second device. The sealing configuration comprises a contact surface comprising a structure configured for increasing a surface pressure when coupling the first device to the second device. The contact surface comprises a metal coating configured for increasing sealing.

In one embodiment, the contact surface encloses a fluid path comprising the first fluid flow path and the second fluid flow path, when the first device couples to the second device.

In one embodiment, the structure comprises one or more indentations, preferably concentric indentations. Alternatively or in addition, the structure may have protrusions, preferably concentric protrusions around the through-hole. Micro-cavities and/or inclusions might be provided in the structure for further acceptance of sealing components or impregnation.

The structure might be or comprise a serrated and/or corrugated profile on at least one side of the sealing surfacing one of the first and second devices.

The structure might be provided using an etching process, preferably applied in a photolithographic process, as readily known in the art.

Each of the first and second devices might be one of a valve, a filter, a pump, a pump head, a fitting, a capillary, or the like as commonly used in HPLC applications.

While the metal coating might cover the entirety of the respective contact surface or even the entirety of the sealing configuration, the metal coating in embodiments might be provided to cover only such part of the respective contact surface, which is configured to provide contact to the respective devices to which it is to seal to. This may mainly depend on the respective process applied for coating and/or the respective application of the seal. In a preferred embodiment, the seal is coated in its entirety with the metal coating.

The metal coating might be a gold coating, preferably a coating of fine gold e.g. having purity higher than 99.9% such as 99.999%. Other materials such as silver or lead might also be used as well as other metal coatings being softer than the material of the support body. The coating material may be selected to be inert (to the fluid applied in the fluid flow path) and/or biocompatible. Gold as coating material has shown excellent properties with respect to inertness as well as biocompatibility.

A thickness (or height) of the coating material is preferably selected and designed not to cover the structure. In other words, the thickness of the coating material is designed so that the surface pressure of the coated structure is still increased over the surface pressure as if it were provided without the structure. Accordingly, the thickness of the coating may be selected to be smaller than a maximum variation in height (or depth) of the structure. This, however, does not apply in a case where the coating is not provided on the entire contact surface but only selectively covers a part of the contact surface in particular where the contact surface abuts to the device, for example on top of protrusions provided by the structure or is not reaching into indentations of the structure In such case, the thickness of the coating is not limited.

The material of the metal coating is preferably selected to fill—when being applied between the first and second devices—smaller surface flaws in the contact surface of the respective device in contact with such metal coating, so that the metal of the coating virtually flows into and thus seals such surface flaws.

In one embodiment, the sealing configuration comprises a seal arranged between the first and the second devices for sealingly coupling the first fluid flow path to the second fluid flow path. The seal comprises a support body having an upper surface, a lower surface, and a through hole between the upper surface and the lower surface, wherein the through hole couples the first fluid flow path to the second fluid flow path when the seal is arranged between the first and the second devices. At least one of the lower surface and the upper surface comprises the structure configured for increasing a surface pressure on the seal, and the at least one of the lower surface and the upper surface comprising the structure further comprises the metal coating configured for increasing sealing.

In one embodiment, each of the lower surface and the upper surface comprises a respective structure configured for increasing surface pressure on the seal. In one embodiment, the structures on the opposing surfaces are substantially mirrored along a plane between the lower and the upper surface, so that the structure of the lower surface is substantially mirrored to the structure of the upper surface.

The support body is preferably made of or comprises a metal material, such as stainless steel (SST). Other suitable materials, such as other metal materials, hard enough not to creep away over time may be applied as well, preferably titanium, tungsten, or alloys such as nickel alloys (e.g., HASTELLOY® nickel alloys commercially available from Haynes International Inc., Kokomo, Ind.). As the material may come in contact with the fluid in the fluid flow path, it should preferably also be selected to be inert to the respective fluid(s) as used.

The through-hole of the seal might comprise a center bore into the support body.

In application when being coupled between the first and second devices, the through-hole provides a fluid flow path between the first and second fluid flow path and sealingly couples the first and second fluid flow path together.

In one embodiment, an HPLC device comprises the first device having the first fluid flow path, the second device having the second fluid flow path, and the sealing configuration according to any of the afore-described embodiments. The sealing configuration is arranged between the first and second devices for sealingly coupling the first and second fluid flow path. The sealing configuration may also be part of at least one of the first and second devices for sealingly coupling the first and second fluid flow path.

In an embodiment, wherein the sealing configuration comprises the seal, the upper surface of the seal can be arranged facing the first device, the lower surface faces the second device, and the through-hole between the upper and lower surfaces couples the first fluid flow path to the second fluid flow path, when the seal is arranged between the first and second devices.

In one embodiment, the sealing configuration is part of a fluid separation system having a fluid flow path configured for separating compounds of a sample fluid in a mobile phase. Such fluid separation system comprises a mobile phase drive (preferably a pumping system) to drive the mobile phase through the fluid flow path. A separation unit (preferably a chromatographic column) is configured for separating compounds of the sample fluid in the mobile phase. In such fluid separation system, a first component has a first portion of the flow path and a second component has a second portion of the fluid flow path. The sealing configuration according to any of the aforedescribed embodiments is arranged between or part of at least one of the first and second components for sealingly coupling the first portion of the fluid flow path to the second portion of the fluid flow path.

The fluid separation system might further comprise one or more of the following components: a sample injector configured to introduce the sample fluid into the mobile phase, a detector configured to detect separated compounds of the sample fluid, a collection unit configured to collect separated compounds of the sample fluid, a data processing unit configured to process data received from the fluid separation system, and/or a degassing apparatus for degassing the mobile phase.

According to an embodiment of the present invention, a seal is provided for an HPLC device. The HPLC device comprises a first device and a second device. The first device has a first fluid flow path, and the second device has a second fluid flow path. The seal is arranged between the first and the second devices and sealingly couples the first fluid flow path to the second fluid flow path. The seal comprises a support body having an upper surface, a lower surface and a through-hole between the upper surface and the lower surface. The through-hole couples the first fluid flow path to the second fluid flow path when the seal is arranged between first and second devices. At least one of the lower surface and the upper surface comprises a structure configured for increasing a surface pressure on the seal. Each of the lower and the upper surfaces, which comprises such structure, further comprises a metal coating configured for increasing sealing. Such a seal is able to be applied in HPLC applications under high pressure of 500-2000 bar and even beyond, where conventional seals are often not suitable enough to reliably seal over a longer timeframe such as plural years. Further, such seals may allow reusing the seals even after several times reopening and closing the coupling.

In one embodiment, a coupling device is configured to sealingly couple to another device. The coupling device has a first fluid flow path. The other device has a second fluid flow path. The coupling device is arranged to the other device for sealingly coupling the first fluid flow path to the second fluid flow path. The coupling device comprises a contact surface having a structure configured for increasing a surface pressure on the other device. The contact surface further has a metal coating for increasing sealing. Such embodiments substantially correspond to the aforementioned embodiments, however with the difference that the sealing features as provided by the seal are now directly provided by the contact surface of the first device. The first device thus integrally "incorporates the seal" of the aforementioned embodiments. Such integrated sealing structure might in particular be of advantage when the coupling device is a replaceable component.

Embodiments of the contact surface may also comprise, mutatis mutandis, embodiments as given above with respect to the structures and the coating.

The coupling device can be part of a fluid separation system having a fluid flow path configured for separating compounds of a sample fluid in a mobile phase. The fluid separation system comprises a mobile phase drive, such as a pumping system, configured to drive the mobile phase through the fluid flow path, and a separation unit, preferably a chromatographic column, configured for separating compounds of the sample fluid in the mobile phase. The coupling device comprises a first portion of the flow path, and another device has a second portion of the fluid flow path. The coupling device is arranged to the other device for sealingly coupling the first portion of flow path to the second portion of the flow path. The aforesaid with respect to embodiments of the fluid separation system apply here accordingly.

While the sealing according to embodiments of the present invention is preferably applied and designed to fit the requirements of high pressure applications in the range of 500-2000 bar in HPLC systems, such seals may also be applied in other applications in particular requiring reliable high pressure sealings.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

One embodiment of an HPLC system comprises a pumping apparatus having a piston for reciprocation in a pump working chamber to compress liquid in the pump working chamber to a high pressure at which compressibility of the liquid becomes noticeable.

One embodiment of an HPLC system comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (e.g. from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column providing the stationary phase. The column might be a glass or steel tube (e.g. with a diameter from 50 μm to 5 mm and a length of 1 cm to 1 m) or a microfluidic column (as disclosed e.g. in EP 1577012 or the Agilent 1200 Series HPLC-Chip/MS System provided by the applicant Agilent Technologies, see e.g. http://www.chem.agilent.com/Scripts/PDS.asp?IPage=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded, bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen, for example, to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic solvent is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particular 50-120 MPa (500 to 1200 bar).

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

DETAILED DESCRIPTION

Figure 1:
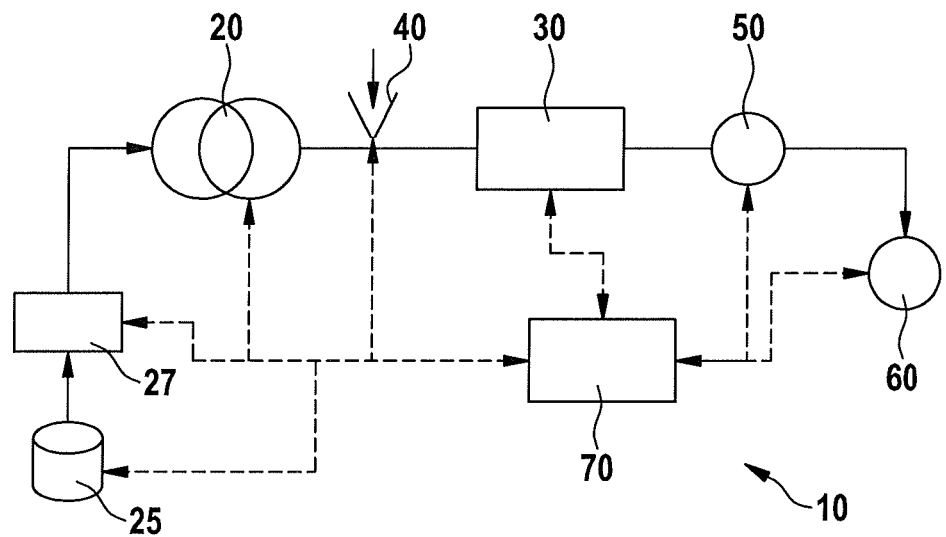
FIG. 1 shows a liquid separation system 10, in accordance with embodiments of the present invention, e.g. used in high performance liquid chromatography (HPLC).

Referring now in greater detail to the drawings, FIG. 1 depicts a general schematic of a liquid separation system 10. A pump 20 receives a mobile phase from a solvent supply 25, typically via a degasser 27, which degasses and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is adapted for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation.

Figure 2:
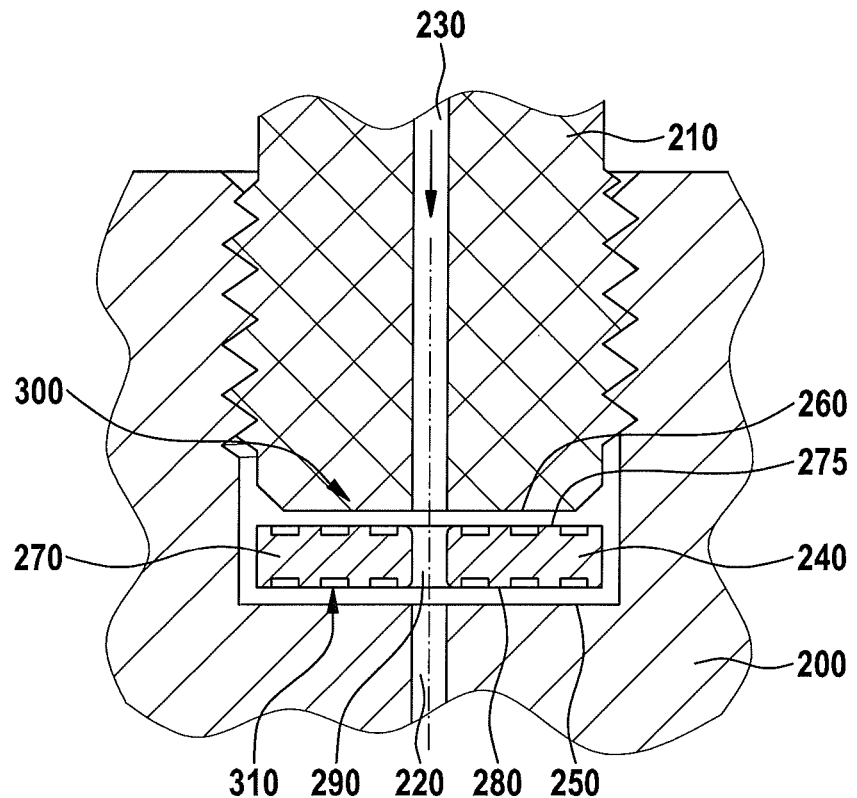
FIG. 2 shows schematically a sealing structure as used in embodiments of the present invention.

FIG. 2 shows schematically a sealing configuration (which might also be referred to as sealing structure) as used in embodiments of the present invention. The sealing configuration may be part of the HPLC system 10 as shown in FIG. 1. While the embodiment of FIG. 2 shows an example for the pump 20, the sealing configuration may also be applied for sealingly coupling other components in the liquid flow path as depicted in FIG. 1.

In the example of FIG. 2, a pump head as a first device 200 is to be sealingly coupled with a second device 210, which may be a valve, filter, fitting, capillary or others. The first device 200 has a flow path 220, and the second device 210 has a flow path 230, which are to be coupled together so that a liquid flowing (e.g. in the direction as indicated by the arrow in FIG. 2) can flow from the flow path 230 to the flow path 220. To avoid leakage in the interface between the first device 200 and second device 210, the sealing configuration comprises a seal 240 arranged between a contact surface 250 of the first device 200 and a contact surface 260 of the second device 210.

The seal 240 has a support body 270 made of a hard metal material, in this example Stainless Steel (SST). The support body 270 has an upper surface 275 facing towards the contact surface 260 of the second device 210. A lower surface 280 of the seal 240 is facing towards the contact surface 250 of the first device 210 (pump head). A through-hole 290 between the upper surface 275 and the lower surface 280 provides a further fluid flow path, which when the first and second devices 200 and 210 are coupled together provide fluid flow path between the first fluid flow path 220 and the second fluid flow path 230.

Figure 3A:
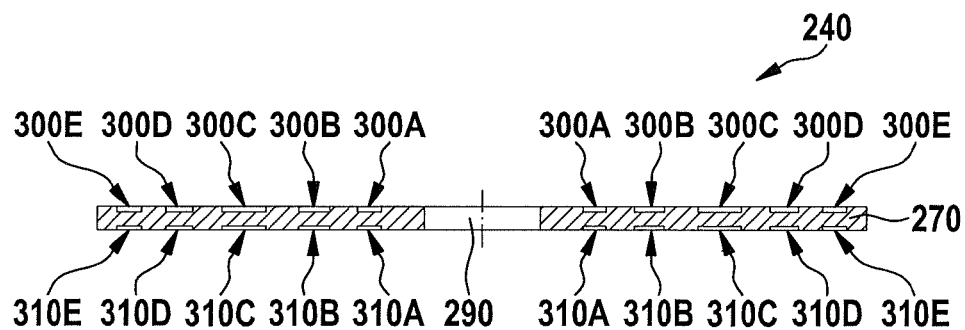
FIG. 3A shows in cross-sectional view and 3B in top view an embodiment of a seal.
Figure 3B:
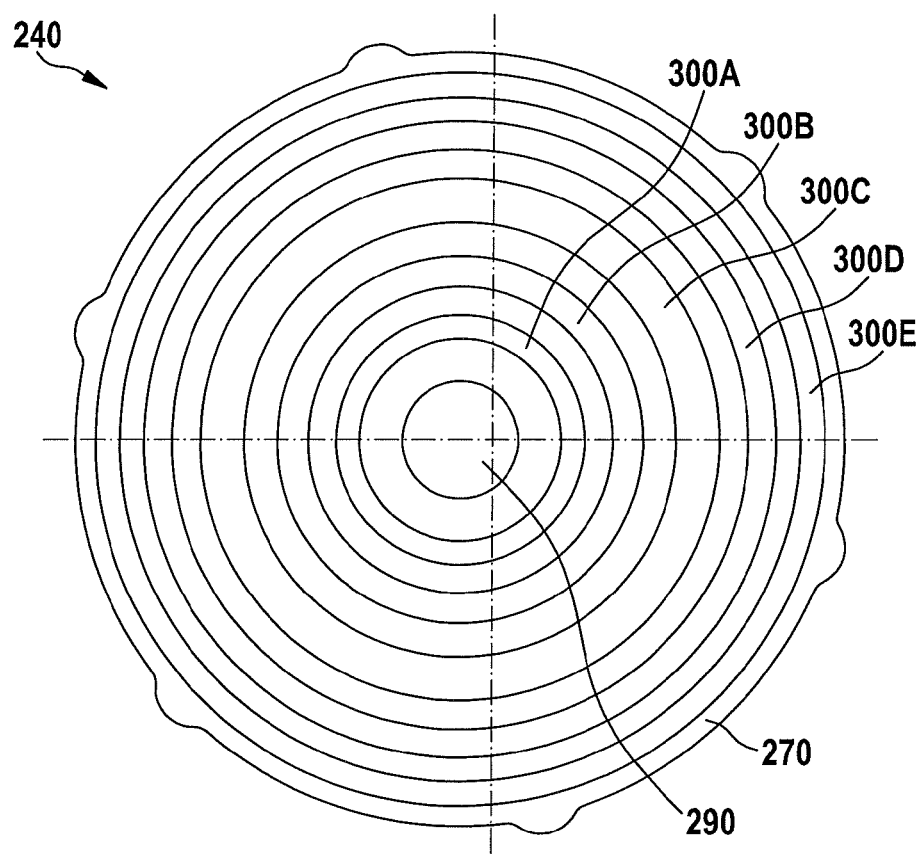

Further shown in FIG. 2 and which is also illustrated in greater detail in FIGS. 3A and 3B, the seal 240 further comprises a structure 300 at its upper surface 275, and a structure 310 at its lower surface 280. The structures 300 and 310 are provided by indentations 300A-300E as well as 310A-310E as can be better seen in FIG. 3A. The indentations are arranged concentrically around the through-hole 290.

In the examples of FIGS. 2 and 3, the upper structure 300 and 310 are symmetric to each other by being mirror-imaged at a plane in the middle between the upper surface 275 and the lower surface 280 of the seal 240. While such symmetric design and arrangement of the structure can increase the sealing properties of the seal 240, other designs are also possible dependent on the respective application. Also, while the concentric arrangement of the indentations is in particular advantageous in rotational symmetric designs, as in the embodiments of FIGS. 2 and 3, any other suitable design of the indentations may also be applied. Further, instead or in addition to the indentations 300A-300E and 310A-310E, one or more protrusions (not shown in the figures) protruding over the respective upper and/or lower surfaces 275 and 280 may be applied, and which may also have (but not necessarily) a concentric design.

In operation, the seal 240 is pressed between the first and second devices 200 and 210, for example by using a thread as indicated in FIG. 2, so that a pressing force is applied on the seal 240. As the structures 300 and 310 lead to a reduced contact area (with respect to the entirety of the surface 275 or 280), this increases surface pressure on the seal 240, thus increasing sealing property of the seal 240.

Figure 4:
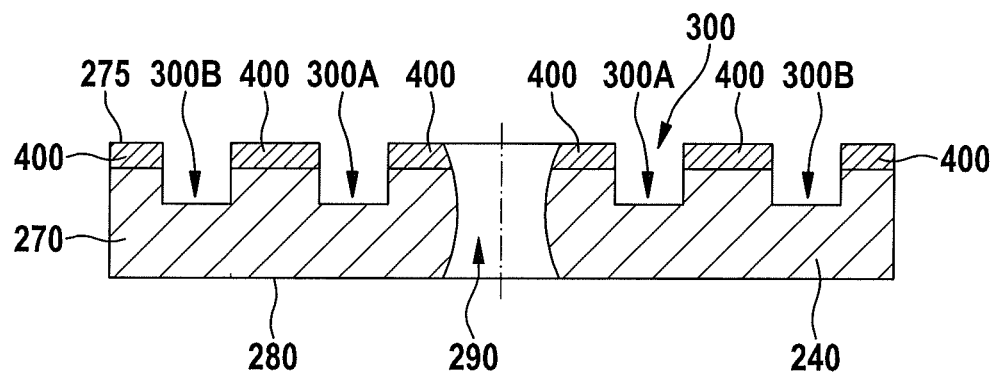
FIG. 4 shows in greater detail and cross-sectional view an embodiment of the seal.

FIG. 4 shows another embodiment of the seal 240 which illustrates that the upper surface 275, which bears the structure 300, further comprises a metal coating 400. The metal coating 400 is also present in the embodiments of FIGS. 2 and 3 but has been omitted in the drawings for the sake of be increasing comprehensibility. The metal coating 400 in the embodiment of FIG. 4 is limited to the upper surface 275 only. In other embodiments, the coating 400 may also extend into the indentations 300A-300B. Further, while the example of FIG. 4 only shows the structure 300 on the upper surface 275, it is clear that the coating 400 can alternatively or in addition be on the lower surface 280 (as in FIGS. 2 and 3), if the seal 240 comprises structures 300 and 310 on the upper surface 275 and/or the lower surface 280.

The metal coating 400 is preferably a coating of gold and in this example of fine gold having purity higher than 99.99%. In application, when the seal 240 is coupled between the first and second devices 200 and 210, the metal coating 400 fills smaller surface flaws at the respective contact surface (contact surfaces 250 and/or 260 in FIG. 2) of the respective device, thus leading to improved sealing properties.

While FIGS. 2 and 4 show the seal 240 in a more schematic view, FIGS. 3a and 3B depict the dimensions of a preferred embodiment. In this example, the seal 240 has a diameter of 8 mm and a thickness of 0.2 mm. The metal coating 400 is provided with a thickness of 0.03 mm gold.

The embodiments of the seal 240 as illustrated in the drawings of FIGS. 2-4 provide an improved sealing in high-pressure HPLC applications, in particular in the pressure range beyond 500 bar. The support body 270 of a harder metal (preferably SST) provides high mechanical stability, while the metal coating 400 (preferably gold) of a metal softer than the material of the support body 270 provides a relatively soft surface which allows smoothing flaws or untightness in the corresponding contact surface of the adjacent device. The structure 300, 310 increases the surface pressure between the adjacent surfaces of the seal 240 and the respective device. Embodiments of the seal 240 can thus reliably seal high pressure HPLC applications in the range of 500-2000 bar (and even beyond) and can also fulfill the requirement of bio-compatibility in case a suitable coating material, such as gold, is used for the metal coating 400.

Figure 5:
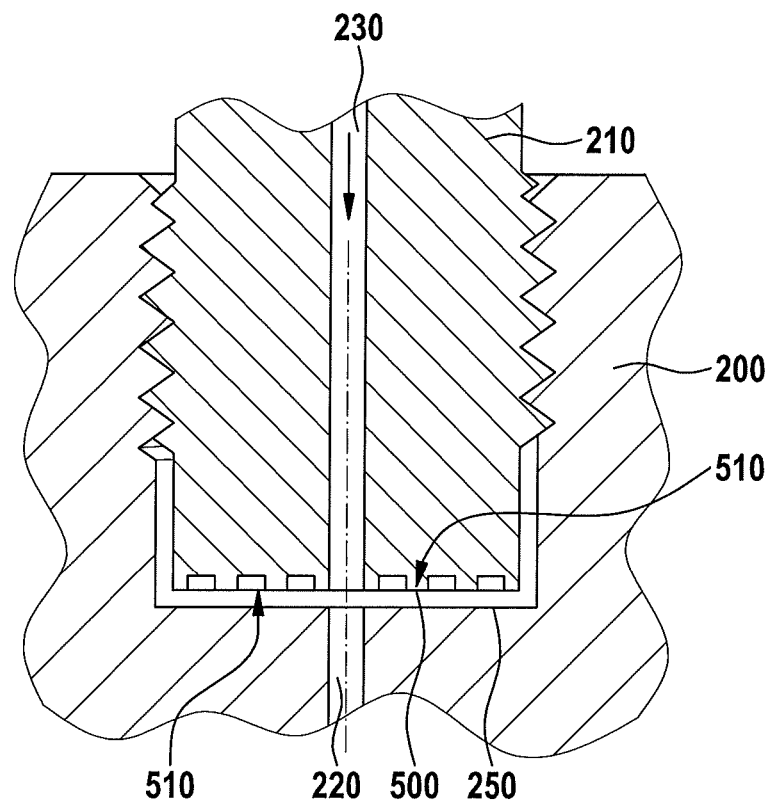
FIG. 5 shows schematically another sealing structure as used in embodiments of the present invention.

FIG. 5 shows schematically another sealing configuration as used in embodiments of the present invention. The embodiment of FIG. 5 substantially corresponds to the embodiment as shown in FIG. 2, however with the difference that the sealing features as provided by the seal 240 (in FIG. 2) are now provided by the second device 210. In other words, the second device 210 in the embodiment of FIG. 5 integrally incorporates the seal 240 of the embodiment of FIG. 2. The sealing configuration of FIG. 5 may also be part of the HPLC system 10 as schematically shown in FIG. 1, and may be applied for sealingly coupling any components in the liquid flow path as depicted in FIG. 1.

In the example of FIG. 5, the pump head 200 (as the first device) is to be sealingly coupled with a second device 210 (which may also be referred to as a coupling device), which may be a valve, filter, fitting, capillary or others. The pump head 200 has the flow path 220, and the second device 210 has the flow path 230, which are to be coupled together so that the liquid flowing (e.g. in the direction as indicated by the arrow in FIG. 2) can flow from the flow path 230 to the flow path 220. To avoid leakage in the interface between the first device 200 and second device 210, the second device 210 is provided with a contact surface 500, which is to be arranged to sealingly abut to the contact surface 250 of the pump head 200.

The contact surface 500 is an integral part of the second device 210. The second device 210, or at least a portion of the second device 210 bearing the contact surface 500 may be made e.g. of a hard metal material, in this example Stainless Steel (SST). The contact surface 500 comprises a structure 510 configured for increasing a surface pressure on the first device 200. The structure 510 can be the same as one of the structures 300 or 310, as illustrated for the seal 240. The contact surface 500, further comprises the metal coating 400 (cf. FIG. 4) configured for increasing sealing. It is clear that the above give illustrations with respect to the structures 300, 310 and the coating 400 also apply, mutatis mutandis, to the contact surface 500 of the embodiment in FIG. 5.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A sealing configuration configured for sealingly coupling a first fluid flow path of a first device to a second fluid flow path of a second device, the sealing configuration comprising:
    a support body comprising an upper surface, a lower surface, and a through hole between the upper surface and the lower surface, wherein the through hole couples the first fluid flow path to the second fluid flow path when the sealing configuration is arranged between the first device and the second device, and at least one of the upper surface and the lower surface comprises a structure configured for increasing a surface pressure when coupling the first device to the second device, the structure comprising one or more indentations; and
    a metal coating configured for increasing sealing, the metal coating disposed between one or more indentations on at least one raised contact surface of at least one of the upper surface and the lower surface on a same side of the support body as the structure, wherein the metal coating comprises a material softer than a material of the support body.

2. The sealing configuration of claim 1, wherein the surface comprising the structure encloses a fluid path comprising the first fluid flow path and the second fluid flow path, when the first device couples to the second device.

3. The sealing configuration of claim 1, wherein the structure comprises at least one of:
    one or more concentric indentations;
    one or more protrusions;
    one or more concentric protrusions;
    one or more micro-cavities for further acceptance of sealing components or impregnation;
    one or more inclusions for further acceptance of sealing components or impregnation;
    a serrated profile on at least one side facing one of the first and the second devices;
    a corrugated profile on at least one side facing one of the first and the second devices.

4. The sealing configuration of claim 1, wherein
    at least one of the first device and the second device is one of: a valve, a filter, a pump, a pump head, a fitting, and a capillary.

5. The sealing configuration of claim 1, comprising at least one of:
    the metal coating covers at least such part of at least one of the upper surface and lower surface that is configured to provide a contact surface to the respective one of the first device and the second device;
    the metal coating comprises a coating of at least one of: gold, fine gold of purity higher than 99.9%, silver, and lead;
    the metal coating is configured to fill surface flaws in a contact surface of the respective one of the first device and the second device.

6. The sealing configuration of claim 1, wherein
    the lower surface and the upper surface each comprise a structure configured for increasing surface pressure on the seal.

7. The sealing configuration of claim 6, wherein
    the structure of the lower surface is substantially mirrored, along a plane between the lower surface and the upper surface, to the structure of the upper surface.

8. The sealing configuration of claim 1, comprising at least one of:
    the support body comprises a metal, stainless steel, titanium, tungsten, an alloy, or a nickel alloy;
    the through hole comprises a center bore;
    the through hole provides a fluid flow path between the first fluid flow path and the second fluid flow path.

9. The sealing configuration of claim 1, wherein the one or more indentations are concentric about the through hole.

10. The sealing configuration of claim 1, wherein the metal coating is disposed only between one or more indentations on at least one contact surface of the upper surface or lower surface.

11. The sealing configuration of claim 1, wherein the structure is a first structure, the upper surface comprises the first structure, and the metal coating is disposed on the upper surface, and further comprising a second structure configured for increasing a surface pressure when coupling the first device to the second device, the second structure comprising one or more indentations.

12. The sealing configuration of claim 11, wherein the metal coating is a first metal coating, and further comprising a second metal coating configured for increasing sealing, the second metal coating disposed on the lower surface, wherein the second metal coating comprises a material softer than a material of the support body.

13. A seal for an HPLC device comprising a first device and a second device, wherein the first device has a first fluid flow path, the second device has a second fluid flow path, and the seal is arranged between the first and the second devices for sealingly coupling the first fluid flow path to the second fluid flow path, the seal comprising
- a support body having an upper surface, a lower surface, and a through hole between the upper surface and the lower surface, wherein the through hole couples the first fluid flow path to the second fluid flow path when the seal is arranged between the first and the second devices,
- wherein at least one of the lower surface and the upper surface comprises a structure configured for increasing a surface pressure on the seal, the structure comprising one or more indentations; and
- the at least one of the lower surface and the upper surface comprising the structure further comprises a metal coating configured for increasing sealing, wherein the metal coating is disposed between one or more indentations on at least one raised contact surface and comprises a material softer than a material of the support body.

14. An HPLC device comprising:
- a first device having a first fluid flow path,
- a second device having a second fluid flow path, and
- a sealing configuration according to claim 1,
- wherein the sealing configuration is arranged between or part of at least one of the first and the second devices for sealingly coupling the first fluid flow path to the second fluid flow path.

15. The HPLC device of claim 14, wherein the sealing configuration comprises the seal of claim 1, wherein
- an upper surface of the seal is facing the first device,
- a lower surface of the seal is facing the second device, and
- a through hole between the upper surface and the lower surface couples the first fluid flow path to the second fluid flow path when the seal is arranged between the first and the second devices.

16. A fluid separation system having a fluid flow path configured for separating compounds of a sample fluid in a mobile phase, the fluid separation system comprising:
- a mobile phase drive, preferably a pumping system, configured to drive the mobile phase through the fluid flow path,
- a separation unit, preferably a chromatographic column, configured for separating compounds of the sample fluid in the mobile phase,
- a first component having a first portion of the flow path,
- a second component having a second portion of the fluid flow path, and
- a sealing configuration according to claim 1, wherein the sealing configuration is arranged between or provided by at least one of the first and the second components for sealingly coupling the first portion of the fluid flow path to the second portion of the fluid flow path.

* * * * *